US006737273B2

(12) United States Patent
Payne et al.

(10) Patent No.: US 6,737,273 B2
(45) Date of Patent: *May 18, 2004

(54) *BACILLUS THURINGIENSIS* ISOLATE ACTIVE AGAINST LEPIDOPTERAN PESTS, AND GENES ENCODING NOVEL LEPIDOPTERAN-ACTIVE TOXINS

(75) Inventors: Jewel Payne, San Diego, CA (US); August J. Sick, Oceanside, CA (US)

(73) Assignee: Myocogen Corporation, Indianapolis, IN (US)

( * ) Notice: Subject to any disclaimer, the term of this patent is extended or adjusted under 35 U.S.C. 154(b) by 34 days.

This patent is subject to a terminal disclaimer.

(21) Appl. No.: 09/837,961

(22) Filed: Apr. 19, 2001

(65) Prior Publication Data

US 2004/0058860 A1 Mar. 25, 2004

Related U.S. Application Data

(60) Division of application No. 09/521,344, filed on Mar. 9, 2000, now Pat. No. 6,573,240, which is a division of application No. 08/933,891, filed on Sep. 19, 1997, now Pat. No. 6,096,708, which is a continuation of application No. 08/356,034, filed on Dec. 14, 1994, now Pat. No. 5,691,308, which is a continuation of application No. 08/210,110, filed on Mar. 17, 1994, now abandoned, which is a continuation of application No. 07/865,168, filed on Apr. 9, 1992, now abandoned, which is a division of application No. 07/451,261, filed on Dec. 14, 1989, now Pat. No. 5,188,960, which is a continuation-in-part of application No. 07/371,955, filed on Jun. 27, 1989, now Pat. No. 5,126,133.

(51) Int. Cl.[7] .............................. C12N 1/00; C12N 5/10; C12N 15/32

(52) U.S. Cl. .................... 435/418; 435/419; 435/252.3; 435/254.11; 435/320.1; 424/93.2; 424/93.461; 536/23.71

(58) Field of Search ........................ 536/23.71; 435/418, 435/419, 252.3, 254.11, 320.1; 424/93.2, 93.461, 93.3

(56) References Cited

U.S. PATENT DOCUMENTS 5,126,133 A  6/1992  Payne et al. ........... 424/96.461
5,164,180 A  11/1992 Payne et al. ........... 424/93.461
5,188,960 A  2/1993  Payne et al. ............ 435/252.3
5,206,166 A  4/1993  Payne et al. ............ 435/252.3
5,246,852 A  9/1993  Payne et al. ........... 435/252.31
5,407,825 A  4/1995  Payne et al. ........... 435/252.34
5,691,308 A  11/1997 Payne et al. .............. 514/12
6,096,708 A  8/2000  Payne et al. .............. 514/12

FOREIGN PATENT DOCUMENTS

AU  0632335   5/1993
EP  0 400 246  5/1990

OTHER PUBLICATIONS

Sutton et al. Synthetic crylllA gene from *Bacillus thuringiensis* improved for high expression in plants. 1992. Transgenic Research vol. 1(5) pp. 228–236.*

Honee et al., "Nucleotide sequence of crystal protein gene isolated from *B. thuringensis* subspecies *entomocidus* 60.5 coding for a toxin highly active against *Spodoptera* species," *Nucleic Acids Research* (1988), p. 6240, vol. 16, Issue 13.

Sanchis et al., "Nucleotide sequence and analysis of the N–terminal coding region of the *Spodoptera*–active δ–endotoxin gene of *Bacillus thuringiensis aizawai* 7.29," *Molecular Microbiology*, 1989, pp. 229–238, vol. 3, Issue 2.

Hofte et al., "Nucleotide sequence and deduced amino acid sequence of a new Lepidoptera–specific crystal protein gene from *Bacillus thuringiensis*," *Nucleic Acids Research*, 1990, p. 5545, vol. 18.

Chambers et al., "Isolation and Characterization of a Novel Insecticidal Crystal Protein Gene from *Bacillus thuringiensis* subsp. *aizawai*," *Journal of Bacteriology*, 1991, pp. 3966–3976, vol. 173, Issue 13.

* cited by examiner

*Primary Examiner*—Gabriele Bugaisky
(74) *Attorney, Agent, or Firm*—Saliwanchik, Lloyd & Saliwanchik

(57) ABSTRACT

Novel *Bacillus thuringiensis* genes encoding toxins which are active against lepidopteran insects have been cloned from novel lepidopteran-active *B. thuringiensis* microbes. The DNA encoding the *B. thuringiensis* toxins can be used to transform various prokaryotic and eukaryotic microbes to express the *B. thuringiensis* toxins. These recombinant microbes can be used to control lepidopteran insects in various environments.

4 Claims, 1 Drawing Sheet

A. *Bacillus thuringiensis* HD-1
B. *Bacillus thuringiensis* PS81I

FIG. 1

SEQUENCE LISTING

<160> NUMBER OF SEQ ID NOS: 10

<210> SEQ ID NO 1
<211> LENGTH: 3528
<212> TYPE: DNA
<213> ORGANISM: Bacillus thuringiensis

<400> SEQUENCE: 1

```
atgaataatc agaatcaatg cgttccttat aactgtttga atgatccgac aattgaaata      60
ttagaaggag aaagaataga aactggttac accccaatag atatttcctt gtcgctaacg     120
caatttctgt tgagtgaatt tgtcccaggt gctgggtttg tattaggttt aattgattta     180
atatgggggt ttgtgggtcc ctctcaatgg gatgcatttc ttgtgcaaat gaacagtta     240 attaaccaaa gaatagagga attcgctagg aaccaagcaa tttctagatt agaagggcta     300
agcaaccttt atcaaattta cgcagaagct tttagagagt gggaagcaga tcctactaat     360
ccagcattaa cagaagagat gcgtattcag ttcaatgaca tgaacagtgc tcttacaacc     420
gctattcctc tttttacagt tcaaaattat caagtacctc ttctatcagt atatgttcaa     480
gctgcaaatt tacatttatc ggttttgaga gatgtttcag tgtttggaca acgttgggga     540
tttgatgtag caacaatcaa tagtcgttat aatgatttaa ctaggcttat tggcacctat     600
acagattatg ctgtacgctg gtataatacg ggattagaac gtgtatgggg accggattct     660
agagattggg taaggtataa tcaatttaga agagagctaa cactaactgt attagatatc     720
gtttctctgt tcccgaacta tgatagtaga acgtatccaa ttcgaacagt ttcccaatta     780
actagagaaa tttatacaaa cccagtatta gaaaattttg atggtagttt tcgtggaatg     840
gctcagagaa tagaacagaa tattaggcaa ccacatctta tggatctcct taatagtata     900 accattttata ctgatgtgca tagaggcttt aattattggt caggacatca aataacagct     960
tctcctgtcg gttttgcggg gccagaattt acttttccta gatatggaac catgggaaat    1020
```

```
gctgctccac cgtactgat ctcaactact ggtttgggga ttttagaac attatcttca    1080 cctctttaca gaagaattat acttggttca ggcccaaata atcagaacct gtttgtcctt    1140
gatggaacgg aattttcttt tgcctccta acagccgatt taccttctac tatatacaga    1200
caaaggggaa cggtcgattc actagatgta ataccgccac aggataatag tgtgccagca    1260
cgtgcgggat ttagtcatcg attaagtcat gttacaatgc tgagccaagc agctggagca    1320
gtttacacct tgagagctcc aacgttttct tggcgacatc gtagtgctga attctctaac    1380
ctaattcctt catcacaaat cacacagata cctttaacaa agtctattaa tcttggctct    1440
gggacctctg ttgttaaagg accaggattt acaggaggag atattcttcg ataacttca    1500 cctggccaga tttcaacctt aagagtgact attacgcac cattatcaca agatatcgc    1560 gtaagaattc gctacgcttc tactacaaat ttacaattcc atacatcaat tgacggaaga    1620
cctattaatc aggggaattt ttcagcaact atgagtagtg ggggtaattt acagtccgga    1680
agctttagga ctgcaggttt tactactccg tttaactttt caaatggatc aagtatattt    1740
acgttaagtg ctcatgtctt caattcaggc aatgaagttt atatagagcg aattgaattt    1800
gttccggcag aagtaacatt tgaggcggaa tatgatttag aaagagcgca agaggcggtg    1860
aatgctctgt ttacttcttc caatcaacta ggattaaaaa caaatgtgac ggactatcat    1920
attgatcaag tgtccaatct agtcgaatgt ttatccggtg aattctgtct ggatgaaaag    1980
agagaattgt ccgagaaagt caaacatgcg aaccgactca gtgatgagcg aatttacttt    2040
caagacccaa acttcagagg catcaataga caaccagacc gtggctggag aggcagtacg    2100
gatattacca tccaaggagg agatgacgta ttcaaagaga attacgtcac actaccgggt    2160
acctttaatg agtgttatcc tacgtatctg tatcaaaaaa tagatgagtc gaaattaaaa    2220 gcctatacccc gttaccaatt aagagggtac atcgaggata gtcaacactt agaaatctat    2280
ttaattcgct acaatacaaa acacgaaaca gtaaatgtgc caggtacggg ttccttatgg    2340
ccgctttcag tcgaaaatcc aattggaaag tgcggagaac caaatcgatg cgcaccacaa    2400
cttgaatgga atcctgatct agattgttcc tgcagagacg gggaaaaatg tgcacatcac    2460
tcccatcatt tctccttgga cattgatatt ggatgtacag atttaaatga gaacttaggt    2520
gtatgggtga tattcaaaat taagatgcaa gatggtcacg caagactagg taatctagag    2580
tttctcgaag agaaaccatt agtaggcgaa tcgttagcac gcgtgaagag agcggagaag    2640
aagtggagag acaaacgaga gaaattgcaa gtggaaacaa atatcgttta taaagaggca    2700
aaagaatctg tagatgcttt atttgtgaac tctcaatatg atagattaca gcggatacc    2760 gacatcgcga tgattcatgc ggcagataaa cgcgttcatc gaattcgaga agcatatctt    2820
ccagagttat ctgtaattcc gggtgtcaat gcgggcattt ttgaagaatt agaggacgt    2880 attttcacag cctactcttt atatgatgcg agaaatgtca ttaaaaatgg cgatttcaat    2940
aatggcttat catgctggaa cgtgaaaggg catgtagatg tagaagaaca aaacaaccac    3000
cgttcggttc ttgttgtccc ggaatgggaa gcagaggtgt cacaagaggt tcgtgtctgt    3060
ccaggtcgtg gctatatcct acgtgttaca gcgtacaaag agggatatgg agaaggttgc    3120
gtaacgattc atgagatcga agacaataca gacgaactga aattcagcaa ctgtgtagaa    3180
gaggaagtat atccaaacaa cacggtaacg tgtaatgatt atactgcaaa tcaagaagaa    3240 tacggggtc cgtacacttc tcgtaatcgt ggatatggtg aatcttatga agtaattct    3300 tccataccag ctgagtatgc gccagtttat gaggaagcat atatagatgg aagaaaagag    3360
```

-continued

```
aatccttgtg aatctaacag aggatatggg gattacacgc cactaccagc tggttatgtg    3420
acaaaagaat tagagtactt cccagaaacc gataaggtat ggattgagat cggggaaacg    3480
gaaggaacat tcatcgtgga tagcgtggaa ttactcctta tggaggaa                 3528
```

<210> SEQ ID NO 2
<211> LENGTH: 1176
<212> TYPE: PRT
<213> ORGANISM: Bacillus thuringiensis

<400> SEQUENCE: 2

```
Met Asn Asn Gln Asn Gln Cys Val Pro Tyr Asn Cys Leu Asn Asp Pro
1               5                   10                  15

Thr Ile Glu Ile Leu Glu Gly Glu Arg Ile Glu Thr Gly Tyr Thr Pro
            20                  25                  30

Ile Asp Ile Ser Leu Ser Leu Thr Gln Phe Leu Leu Ser Glu Phe Val
        35                  40                  45

Pro Gly Ala Gly Phe Val Leu Gly Leu Ile Asp Leu Ile Trp Gly Phe
    50                  55                  60

Val Gly Pro Ser Gln Trp Asp Ala Phe Leu Val Gln Ile Glu Gln Leu
65                  70                  75                  80

Ile Asn Gln Arg Ile Glu Glu Phe Ala Arg Asn Gln Ala Ile Ser Arg
                85                  90                  95

Leu Glu Gly Leu Ser Asn Leu Tyr Gln Ile Tyr Ala Glu Ala Phe Arg
            100                 105                 110

Glu Trp Glu Ala Asp Pro Thr Asn Pro Ala Leu Thr Glu Glu Met Arg
        115                 120                 125

Ile Gln Phe Asn Asp Met Asn Ser Ala Leu Thr Thr Ala Ile Pro Leu
    130                 135                 140

Phe Thr Val Gln Asn Tyr Gln Val Pro Leu Leu Ser Val Tyr Val Gln
145                 150                 155                 160

Ala Ala Asn Leu His Leu Ser Val Leu Arg Asp Val Ser Val Phe Gly
                165                 170                 175

Gln Arg Trp Gly Phe Asp Val Ala Thr Ile Asn Ser Arg Tyr Asn Asp
            180                 185                 190

Leu Thr Arg Leu Ile Gly Thr Tyr Thr Asp Tyr Ala Val Arg Trp Tyr
        195                 200                 205

Asn Thr Gly Leu Glu Arg Val Trp Gly Pro Asp Ser Arg Asp Trp Val
    210                 215                 220

Arg Tyr Asn Gln Phe Arg Arg Glu Leu Thr Leu Thr Val Leu Asp Ile
225                 230                 235                 240

Val Ser Leu Phe Pro Asn Tyr Asp Ser Arg Thr Tyr Pro Ile Arg Thr
                245                 250                 255

Val Ser Gln Leu Thr Arg Glu Ile Tyr Thr Asn Pro Val Leu Glu Asn
            260                 265                 270

Phe Asp Gly Ser Phe Arg Gly Met Ala Gln Arg Ile Glu Gln Asn Ile
        275                 280                 285

Arg Gln Pro His Leu Met Asp Leu Leu Asn Ser Ile Thr Ile Tyr Thr
    290                 295                 300

Asp Val His Arg Gly Phe Asn Tyr Trp Ser Gly His Gln Ile Thr Ala
305                 310                 315                 320

Ser Pro Val Gly Phe Ala Gly Pro Glu Phe Thr Phe Pro Arg Tyr Gly
                325                 330                 335

Thr Met Gly Asn Ala Ala Pro Pro Val Leu Ile Ser Thr Thr Gly Leu
            340                 345                 350
```

-continued

```
Gly Ile Phe Arg Thr Leu Ser Ser Pro Leu Tyr Arg Arg Ile Ile Leu
        355                 360                 365

Gly Ser Gly Pro Asn Asn Gln Asn Leu Phe Val Leu Asp Gly Thr Glu
        370                 375                 380

Phe Ser Phe Ala Ser Leu Thr Ala Asp Leu Pro Ser Thr Ile Tyr Arg
385                 390                 395                 400

Gln Arg Gly Thr Val Asp Ser Leu Asp Val Ile Pro Pro Gln Asp Asn
                405                 410                 415

Ser Val Pro Ala Arg Ala Gly Phe Ser His Arg Leu Ser His Val Thr
                420                 425                 430

Met Leu Ser Gln Ala Ala Gly Ala Val Tyr Thr Leu Arg Ala Pro Thr
        435                 440                 445

Phe Ser Trp Arg His Arg Ser Ala Glu Phe Ser Asn Leu Ile Pro Ser
        450                 455                 460

Ser Gln Ile Thr Gln Ile Pro Leu Thr Lys Ser Ile Asn Leu Gly Ser
465                 470                 475                 480

Gly Thr Ser Val Val Lys Gly Pro Gly Phe Thr Gly Gly Asp Ile Leu
                485                 490                 495

Arg Ile Thr Ser Pro Gly Gln Ile Ser Thr Leu Arg Val Thr Ile Thr
                500                 505                 510

Ala Pro Leu Ser Gln Arg Tyr Arg Val Arg Ile Arg Tyr Ala Ser Thr
        515                 520                 525

Thr Asn Leu Gln Phe His Thr Ser Ile Asp Gly Arg Pro Ile Asn Gln
        530                 535                 540

Gly Asn Phe Ser Ala Thr Met Ser Ser Gly Gly Asn Leu Gln Ser Gly
545                 550                 555                 560

Ser Phe Arg Thr Ala Gly Phe Thr Thr Pro Phe Asn Phe Ser Asn Gly
                565                 570                 575

Ser Ser Ile Phe Thr Leu Ser Ala His Val Phe Asn Ser Gly Asn Glu
                580                 585                 590

Val Tyr Ile Glu Arg Ile Glu Phe Val Pro Ala Glu Val Thr Phe Glu
        595                 600                 605

Ala Glu Tyr Asp Leu Glu Arg Ala Gln Glu Ala Val Asn Ala Leu Phe
        610                 615                 620

Thr Ser Ser Asn Gln Leu Gly Leu Lys Thr Asn Val Thr Asp Tyr His
625                 630                 635                 640

Ile Asp Gln Val Ser Asn Leu Val Glu Cys Leu Ser Gly Glu Phe Cys
                645                 650                 655

Leu Asp Glu Lys Arg Glu Leu Ser Glu Lys Val Lys His Ala Asn Arg
                660                 665                 670

Leu Ser Asp Glu Arg Asn Leu Leu Gln Asp Pro Asn Phe Arg Gly Ile
        675                 680                 685

Asn Arg Gln Pro Asp Arg Gly Trp Arg Gly Ser Thr Asp Ile Thr Ile
        690                 695                 700

Gln Gly Gly Asp Asp Val Phe Lys Glu Asn Tyr Val Thr Leu Pro Gly
705                 710                 715                 720

Thr Phe Asn Glu Cys Tyr Pro Thr Tyr Leu Tyr Gln Lys Ile Asp Glu
                725                 730                 735

Ser Lys Leu Lys Ala Tyr Thr Arg Tyr Gln Leu Arg Gly Tyr Ile Glu
                740                 745                 750

Asp Ser Gln His Leu Glu Ile Tyr Leu Ile Arg Tyr Asn Thr Lys His
        755                 760                 765
```

-continued

```
Glu Thr Val Asn Val Pro Gly Thr Gly Ser Leu Trp Pro Leu Ser Val
770                 775                 780

Glu Asn Pro Ile Gly Lys Cys Gly Glu Pro Asn Arg Cys Ala Pro Gln
785                 790                 795                 800

Leu Glu Trp Asn Pro Asp Leu Asp Cys Ser Cys Arg Asp Gly Glu Lys
                805                 810                 815

Cys Ala His His Ser His His Phe Ser Leu Asp Ile Asp Ile Gly Cys
                820                 825                 830

Thr Asp Leu Asn Glu Asn Leu Gly Val Trp Val Ile Phe Lys Ile Lys
                835                 840                 845

Met Gln Asp Gly His Ala Arg Leu Gly Asn Leu Glu Phe Leu Glu Glu
850                 855                 860

Lys Pro Leu Val Gly Glu Ser Leu Ala Arg Val Lys Arg Ala Glu Lys
865                 870                 875                 880

Lys Trp Arg Asp Lys Arg Glu Lys Leu Gln Val Glu Thr Asn Ile Val
                885                 890                 895

Tyr Lys Glu Ala Lys Glu Ser Val Asp Ala Leu Phe Val Asn Ser Gln
                900                 905                 910

Tyr Asp Arg Leu Gln Ala Asp Thr Asp Ile Ala Met Ile His Ala Ala
                915                 920                 925

Asp Lys Arg Val His Arg Ile Arg Glu Ala Tyr Leu Pro Glu Leu Ser
930                 935                 940

Val Ile Pro Gly Val Asn Ala Gly Ile Phe Glu Glu Leu Glu Gly Arg
945                 950                 955                 960

Ile Phe Thr Ala Tyr Ser Leu Tyr Asp Ala Arg Asn Val Ile Lys Asn
                965                 970                 975

Gly Asp Phe Asn Asn Gly Leu Ser Cys Trp Asn Val Lys Gly His Val
                980                 985                 990

Asp Val Glu Glu Gln Asn Asn His Arg Ser Val Leu Val Val Pro Glu
                995                 1000                1005

Trp Glu Ala Glu Val Ser Gln Glu Val Arg Val Cys Pro Gly Arg
    1010                1015                1020

Gly Tyr Ile Leu Arg Val Thr Ala Tyr Lys Glu Gly Tyr Gly Glu
    1025                1030                1035

Gly Cys Val Thr Ile His Glu Ile Glu Asp Asn Thr Asp Glu Leu
    1040                1045                1050

Lys Phe Ser Asn Cys Val Glu Glu Val Tyr Pro Asn Asn Thr
    1055                1060                1065

Val Thr Cys Asn Asp Tyr Thr Ala Asn Gln Glu Glu Tyr Gly Gly
    1070                1075                1080

Ala Tyr Thr Ser Arg Asn Arg Gly Tyr Gly Glu Ser Tyr Glu Ser
    1085                1090                1095

Asn Ser Ser Ile Pro Ala Glu Tyr Ala Pro Val Tyr Glu Glu Ala
    1100                1105                1110

Tyr Ile Asp Gly Arg Lys Glu Asn Pro Cys Glu Ser Asn Arg Gly
    1115                1120                1125

Tyr Gly Asp Tyr Thr Pro Leu Pro Ala Gly Tyr Val Thr Lys Glu
    1130                1135                1140

Leu Glu Tyr Phe Pro Glu Thr Asp Lys Val Trp Ile Glu Ile Gly
    1145                1150                1155

Glu Thr Glu Gly Thr Phe Ile Val Asp Ser Val Glu Leu Leu Leu
    1160                1165                1170

Met Glu Glu
```

1175

<210> SEQ ID NO 3
<211> LENGTH: 3495
<212> TYPE: DNA
<213> ORGANISM: Bacillus thuringiensis

<400> SEQUENCE: 3

```
atggaaataa ataatcaaaa ccaatgtgtg ccttacaatt gtttaagtaa tcctaaggag      60
ataatattag gcgaggaaag gctagaaaca gggaatactg tagcagacat ttcattaggg     120
cttattaatt ttctatattc taattttgta ccaggaggag gatttatagt aggtttacta     180
gaattaatat ggggatttat agggccttcg caatgggata tttttttagc tcaaattgag     240
caattgatta gtcaaagaat agaagaattt gctaggaatc aggcaatttc aagattggag     300
gggctaagca atctttataa ggtctatgtt agagcgttta gcgactggga gaaagatcct     360
actaatcctg ctttaaggga gaaatgcgt atacaattta atgacatgaa tagtgctctc     420
ataacggcta ttccactttt tagagttcaa aattatgaag ttgctctttt atctgtatat     480
gttcaagccg caaacttaca tttatctatt ttaagggatg tttcagtttt cggagaaaga     540
tggggatatg atacagcgac tatcaataat cgctatagtg atctgactag ccttattcat     600
gtttatacta accattgtgt ggatacgtat aatcagggat taaggcgttt ggaaggtcgt     660
tttcttagcg attggattgt atataatcgt ttccggagac aattgacaat tcagtatta      720 gatattgttg cgttttttcc aaattatgat attagaacat atccaattca aacagctact     780
cagctaacga gggaagtcta tctggattta cctttattta tgaaaatct ttctcctgca      840 gcaagctatc aacctttc agctgctgaa agtgctataa ttagaagtcc tcatttagta      900 gacttttaa atagctttac catttataca gatagtctgg cacgttatgc atattgggga     960
gggcacttgg taaattcttt ccgcacagga accactacta atttgataag atcccctta     1020 tatggaaggg aaggaaatac agagcgcccc gtaactatta ccgcatcacc tagcgtacca     1080
atatttagaa cactttcata tattacaggc cttgacaatt caaatcctgt agctggaatc     1140
gagggagtgg aattccaaaa tactataagt agaagtatct atcgtaaaag cggtccaata     1200 gattcttta gtgaattacc acctcaagat gccagcgtat ctcctgcaat tgggtatagt     1260
caccgtttat gccatgcaac atttttagaa cggattagtg accaagaat agcaggcacc     1320 gtattttctt ggacacaccg tagtgccagc cctactaatg aagtaagtcc atctagaatt     1380
acacaaattc catgggtaaa ggcgcatact cttgcatctg gtgcctccgt cattaaaggt     1440
cctggattta caggtggaga tattctgact aggaatagta tgggcgagct ggggacctta     1500
cgagtaacct tcacaggaag attaccacaa agttattata cgtttccg ttatgcttcg      1560 gtagcaaata ggagtggtac atttagatat tcacagccac cttcgtatgg aatttcattt     1620
ccaaaaacta tggacgcagg tgaaccacta acatctcgtt cgttcgctca tacaacactc     1680
ttcactccaa taacctttc acgagctcaa gaagaatttg atctatacat ccaatcgggt     1740
gtttatatag atcgaattga atttataccg gttactgcaa catttgaggc agaatatgat     1800 ttagaaaagag cgcaaaaggt ggtgaatgcc ctgtttacgt ctacaaacca actagggcta     1860
aaaacagatg tgacggatta tcatattgat caggtatcca atctagttgc gtgttatcg     1920 gatgaattt gtctgatga aagagagaa ttgtccgaga aagttaaaca tgcaaagcga     1980
ctcagtgatg agcggaattt acttcaagat ccaaacttca gagggatcaa taggcaacca     2040
gaccgtggct ggagaggaag tacggatatt actatccaag gaggagatga cgtattcaaa     2100
```

-continued

```
gagaattacg ttacgctacc gggtaccttt gatgagtgct atccaacgta tttatatcaa    2160
aaaatagatg agtcgaaatt aaaagcctat acccgttatc aattaagagg gtatatcgaa    2220
gatagtcaag acttagaaat ctatttaatt cgttacaatg caaaacacga aatagtaaat    2280
gtaccaggta caggaagttt atggcctctt tctgtagaaa atcaaattgg accttgtgga    2340
gaaccgaatc gatgcgcgcc acaccttgaa tggaatcctg atttacactg ttcctgcaga    2400
gacggggaaa aatgtgcaca tcattctcat catttctctt tggacattga tgttggatgt    2460
acagacttaa atgaggactt aggtgtatgg gtgatattca agattaagac gcaagatggc    2520
cacgcacgac tagggaatct agagtttctc gaagagaaac cattattagg agaagcacta    2580
gctcgtgtga aaagagcgga gaaaaatgg agagacaaac gcgaaacatt acaattggaa    2640
acaactatcg tttataaaga ggcaaaagaa tctgtagatg ctttatttgt aaactctcaa    2700
tatgatagat acaagcggga tacgaacatc gcgatgattc atgcggcaga taacgcgtt     2760 catagaattc gagaagcgta tctgccggag ctgtctgtga ttccgggtgt caatgcggct    2820 attttttgaag aattagaaga gcgtattttc actgcatttt ccctatatga tgcgagaaat    2880
attattaaaa atggcgattt caataatggc ttattatgct ggaacgtgaa agggcatgta    2940
gaggtagaag aacaaaacaa tcaccgttca gtcctggtta tcccagaatg ggaggcagaa    3000
gtgtcacaag aggttcgtgt ctgtccaggt cgtggctata tccttcgtgt tacagcgtac    3060
aaagagggat atggagaagg ttgcgtaacg atccatgaga tcgagaacaa tacagacgaa    3120
ctgaaattca caactgtgt agaagaggaa gtatatccaa caacacggt aacgtgtatt      3180 aattatactg cgactcaaga agaatatgag ggtacgtaca cttctcgtaa tcgaggatat    3240
gacgaagcct atggtaataa cccttccgta ccagctgatt atgcgtcagt ctatgaagaa    3300
aaatcgtata cagatagacg aagagagaat ccttgtgaat ctaacagagg atatggagat    3360
tacacaccac taccagctgg ttatgtaaca aaggaattag agtacttccc agagaccgat    3420
aaggtatgga ttgagattgg agaaacagaa ggaacattca tcgtggacag cgtggaatta    3480
ctccttatgg aggaa                                                    3495
```

<210> SEQ ID NO 4
<211> LENGTH: 1165
<212> TYPE: PRT
<213> ORGANISM: Bacillus thuringiensis

<400> SEQUENCE: 4

Met Glu Ile Asn Asn Gln Asn Gln Cys Val Pro Tyr Asn Cys Leu Ser
1               5                   10                  15

Asn Pro Lys Glu Ile Ile Leu Gly Glu Glu Arg Leu Glu Thr Gly Asn
20 25 30

Thr Val Ala Asp Ile Ser Leu Gly Leu Ile Asn Phe Leu Tyr Ser Asn
35 40 45

Phe Val Pro Gly Gly Gly Phe Ile Val Gly Leu Leu Glu Leu Ile Trp
50 55 60

Gly Phe Ile Gly Pro Ser Gln Trp Asp Ile Phe Leu Ala Gln Ile Glu
65 70 75 80

Gln Leu Ile Ser Gln Arg Ile Glu Glu Phe Ala Arg Asn Gln Ala Ile
85 90 95

Ser Arg Leu Glu Gly Leu Ser Asn Leu Tyr Lys Val Tyr Val Arg Ala
100 105 110

Phe Ser Asp Trp Glu Lys Asp Pro Thr Asn Pro Ala Leu Arg Glu Glu

```
            115                 120                 125
Met Arg Ile Gln Phe Asn Asp Met Asn Ser Ala Leu Ile Thr Ala Ile
    130                 135                 140
Pro Leu Phe Arg Val Gln Asn Tyr Glu Val Ala Leu Leu Ser Val Tyr
145                 150                 155                 160
Val Gln Ala Ala Asn Leu His Leu Ser Ile Leu Arg Asp Val Ser Val
                165                 170                 175
Phe Gly Glu Arg Trp Gly Tyr Asp Thr Ala Thr Ile Asn Asn Arg Tyr
                180                 185                 190
Ser Asp Leu Thr Ser Leu Ile His Val Tyr Thr Asn His Cys Val Asp
                195                 200                 205
Thr Tyr Asn Gln Gly Leu Arg Arg Leu Glu Gly Arg Phe Leu Ser Asp
    210                 215                 220
Trp Ile Val Tyr Asn Arg Phe Arg Arg Gln Leu Thr Ile Ser Val Leu
225                 230                 235                 240
Asp Ile Val Ala Phe Phe Pro Asn Tyr Asp Ile Arg Thr Tyr Pro Ile
                245                 250                 255
Gln Thr Ala Thr Gln Leu Thr Arg Glu Val Tyr Leu Asp Leu Pro Phe
                260                 265                 270
Ile Asn Glu Asn Leu Ser Pro Ala Ala Ser Tyr Pro Thr Phe Ser Ala
    275                 280                 285
Ala Glu Ser Ala Ile Ile Arg Ser Pro His Leu Val Asp Phe Leu Asn
    290                 295                 300
Ser Phe Thr Ile Tyr Thr Asp Ser Leu Ala Arg Tyr Ala Tyr Trp Gly
305                 310                 315                 320
Gly His Leu Val Asn Ser Phe Arg Thr Gly Thr Thr Thr Asn Leu Ile
                325                 330                 335
Arg Ser Pro Leu Tyr Gly Arg Glu Gly Asn Thr Glu Arg Pro Val Thr
                340                 345                 350
Ile Thr Ala Ser Pro Ser Val Pro Ile Phe Arg Thr Leu Ser Tyr Ile
                355                 360                 365
Thr Gly Leu Asp Asn Ser Asn Pro Val Ala Gly Ile Glu Gly Val Glu
    370                 375                 380
Phe Gln Asn Thr Ile Ser Arg Ser Ile Tyr Arg Lys Ser Gly Pro Ile
385                 390                 395                 400
Asp Ser Phe Ser Glu Leu Pro Pro Gln Asp Ala Ser Val Ser Pro Ala
                405                 410                 415
Ile Gly Tyr Ser His Arg Leu Cys His Ala Thr Phe Leu Glu Arg Ile
                420                 425                 430
Ser Gly Pro Arg Ile Ala Gly Thr Val Phe Ser Trp Thr His Arg Ser
    435                 440                 445
Ala Ser Pro Thr Asn Glu Val Ser Pro Ser Arg Ile Thr Gln Ile Pro
    450                 455                 460
Trp Val Lys Ala His Thr Leu Ala Ser Gly Ala Ser Val Ile Lys Gly
465                 470                 475                 480
Pro Gly Phe Thr Gly Gly Asp Ile Leu Thr Arg Asn Ser Met Gly Glu
                485                 490                 495
Leu Gly Thr Leu Arg Val Thr Phe Thr Gly Arg Leu Pro Gln Ser Tyr
                500                 505                 510
Tyr Ile Arg Phe Arg Tyr Ala Ser Val Ala Asn Arg Ser Gly Thr Phe
                515                 520                 525
Arg Tyr Ser Gln Pro Pro Ser Tyr Gly Ile Ser Phe Pro Lys Thr Met
    530                 535                 540
```

```
Asp Ala Gly Glu Pro Leu Thr Ser Arg Ser Phe Ala His Thr Thr Leu
545                 550                 555                 560

Phe Thr Pro Ile Thr Phe Ser Arg Ala Gln Glu Glu Phe Asp Leu Tyr
            565                 570                 575

Ile Gln Ser Gly Val Tyr Ile Asp Arg Ile Glu Phe Ile Pro Val Thr
                580                 585                 590

Ala Thr Phe Glu Ala Glu Tyr Asp Leu Glu Arg Ala Gln Lys Val Val
            595                 600                 605

Asn Ala Leu Phe Thr Ser Thr Asn Gln Leu Gly Leu Lys Thr Asp Val
610                 615                 620

Thr Asp Tyr His Ile Asp Gln Val Ser Asn Leu Val Ala Cys Leu Ser
625                 630                 635                 640

Asp Glu Phe Cys Leu Asp Glu Lys Arg Glu Leu Ser Glu Lys Val Lys
                645                 650                 655

His Ala Lys Arg Leu Ser Asp Glu Arg Asn Leu Leu Gln Asp Pro Asn
            660                 665                 670

Phe Arg Gly Ile Asn Arg Gln Pro Asp Arg Gly Trp Arg Gly Ser Thr
            675                 680                 685

Asp Ile Thr Ile Gln Gly Gly Asp Asp Val Phe Lys Glu Asn Tyr Val
690                 695                 700

Thr Leu Pro Gly Thr Phe Asp Glu Cys Tyr Pro Thr Tyr Leu Tyr Gln
705                 710                 715                 720

Lys Ile Asp Glu Ser Lys Leu Lys Ala Tyr Thr Arg Tyr Gln Leu Arg
                725                 730                 735

Gly Tyr Ile Glu Asp Ser Gln Asp Leu Glu Ile Tyr Leu Ile Arg Tyr
            740                 745                 750

Asn Ala Lys His Glu Ile Val Asn Val Pro Gly Thr Gly Ser Leu Trp
755                 760                 765

Pro Leu Ser Val Glu Asn Gln Ile Gly Pro Cys Gly Glu Pro Asn Arg
            770                 775                 780

Cys Ala Pro His Leu Glu Trp Asn Pro Asp Leu His Cys Ser Cys Arg
785                 790                 795                 800

Asp Gly Glu Lys Cys Ala His His Ser His His Phe Ser Leu Asp Ile
                805                 810                 815

Asp Val Gly Cys Thr Asp Leu Asn Glu Asp Leu Gly Val Trp Val Ile
            820                 825                 830

Phe Lys Ile Lys Thr Gln Asp Gly His Ala Arg Leu Gly Asn Leu Glu
            835                 840                 845

Phe Leu Glu Glu Lys Pro Leu Leu Gly Glu Ala Leu Ala Arg Val Lys
850                 855                 860

Arg Ala Glu Lys Lys Trp Arg Asp Lys Arg Glu Thr Leu Gln Leu Glu
865                 870                 875                 880

Thr Thr Ile Val Tyr Lys Glu Ala Lys Glu Ser Val Asp Ala Leu Phe
                885                 890                 895

Val Asn Ser Gln Tyr Asp Arg Leu Gln Ala Asp Thr Asn Ile Ala Met
            900                 905                 910

Ile His Ala Ala Asp Lys Arg Val His Arg Ile Arg Glu Ala Tyr Leu
            915                 920                 925

Pro Glu Leu Ser Val Ile Pro Gly Val Asn Ala Ala Ile Phe Glu Glu
            930                 935                 940

Leu Glu Gly Arg Ile Phe Thr Ala Phe Ser Leu Tyr Asp Ala Arg Asn
945                 950                 955                 960
```

-continued

```
Ile Ile Lys Asn Gly Asp Phe Asn Asn Gly Leu Leu Cys Trp Asn Val
                965                 970                 975

Lys Gly His Val Glu Val Glu Glu Gln Asn Asn His Arg Ser Val Leu
            980                 985                 990

Val Ile Pro Glu Trp Glu Ala Glu  Val Ser Gln Glu Val  Arg Val Cys
        995                 1000                 1005

Pro Gly  Arg Gly Tyr Ile Leu  Arg Val Thr Ala Tyr  Lys Glu Gly
    1010                 1015                 1020

Tyr Gly  Glu Gly Cys Val Thr  Ile His Glu Ile Glu  Asn Asn Thr
    1025                 1030                 1035

Asp Glu  Leu Lys Phe Asn Asn  Cys Val Glu Glu Glu  Val Tyr Pro
    1040                 1045                 1050

Asn Asn  Thr Val Thr Cys Ile  Asn Tyr Thr Ala Thr  Gln Glu Glu
    1055                 1060                 1065

Tyr Glu  Gly Thr Tyr Thr Ser  Arg Asn Arg Gly Tyr  Asp Glu Ala
    1070                 1075                 1080

Tyr Gly  Asn Asn Pro Ser Val  Pro Ala Asp Tyr Ala  Ser Val Tyr
    1085                 1090                 1095

Glu Glu  Lys Ser Tyr Thr Asp  Arg Arg Arg Glu Asn  Pro Cys Glu
    1100                 1105                 1110

Ser Asn  Arg Gly Tyr Gly Asp  Tyr Thr Pro Leu Pro  Ala Gly Tyr
    1115                 1120                 1125

Val Thr  Lys Glu Leu Glu Tyr  Phe Pro Glu Thr Asp  Lys Val Trp
    1130                 1135                 1140

Ile Glu  Ile Gly Glu Thr Glu  Gly Thr Phe Ile Val  Asp Ser Val
    1145                 1150                 1155

Glu Leu  Leu Leu Met Glu Glu
    1160                 1165
```

<210> SEQ ID NO 5
<211> LENGTH: 3567
<212> TYPE: DNA
<213> ORGANISM: Bacillus thuringiensis

<400> SEQUENCE: 5

```
atggaggaaa ataatcaaaa tcaatgcata ccttacaatt gtttaagtaa tcctgaagaa      60
gtacttttgg atggagaacg gatatcaact ggtaattcat caattgatat ttctctgtca     120
cttgttcagt ttctggtatc taactttgta ccagggggag gatttttagt tggattaata     180
gattttgtat ggggaatagt tggcccttct caatgggatg catttctagt acaaattgaa     240
caattaatta atgaaagaat agctgaattt gctaggaatg ctgctattgc taatttagaa     300
ggattaggaa acaatttcaa tatatatgtg gaagcattta aagaatggga agaagatcct     360
aataatccag caaccaggac cagagtaatt gatcgctttc gtatacttga tgggctactt     420
gaaagggaca ttccttcgtt tcgaatttct ggatttgaag taccccttt atccgtttat     480 gctcaagcgg ccaatctgca tctagctata ttaagagatt ctgtaatttt tggagaaaga     540
tggggattga caacgataaa tgtcaatgaa aactataata gactaattag gcatattgat     600
gaatatgctg atcactgtgc aaatacgtat aatcggggat taaataattt accgaaatct     660
acgtatcaag attggataac atataatcga ttacggagag acttaacatt gactgtatta     720
gatatcgccg ctttctttcc aaactatgac aataggagat atccaattca gccagttggt     780
caactaacaa gggaagttta tacggaccca ttaattaatt ttaatccaca gttacagtct     840
gtagctcaat tacctacttt taacgttatg gagagcagcg caattagaaa tcctcattta     900
```

-continued

```
tttgatatat tgaataatct tacaatcttt acggattggt ttagtgttgg acgcaatttt      960
tattggggag gacatcgagt aatatctagc cttataggag gtggtaacat aacatctcct     1020
atatatggaa gagaggcgaa ccaggagcct ccaagatcct ttacttttaa tggaccggta     1080
tttaggactt tatcaaatcc tactttacga ttattacagc aaccttggcc agcgccacca     1140
tttaatttac gtggtgttga aggagtagaa ttttctacac ctacaaatag ctttacgtat     1200
cgaggaagag gtcaggttga ttctttaact gaattaccgc ctgaggataa tagtgtgcca     1260
cctcgcgaag gatatagtca tcgtttatgt catgcaactt ttgttcaaag atctggaaca     1320
ccttttttaa caactggtgt agtatttttct tggacgcatc gtagtgcaac tcttacaaat     1380
acaattgatc cagagagaat taatcaaata cctttagtga aaggatttag agtttggggg     1440
ggcacctctg tcattacagg accaggattt acaggagggg atatccttcg aagaaatacc     1500
tttggtgatt ttgtatctct acaagtcaat attaattcac caattaccca agataccgt      1560 ttaagatttc gttacgcttc cagtagggat gcacgagtta tagtattaac aggagcggca     1620
tccacaggag tgggaggcca agttagtgta aatatgcctc ttcagaaaac tatggaaata     1680
ggggagaact taacatctag aacatttaga tataccgatt ttagtaatcc ttttcatttt      1740
agagctaatc cagatataat tgggataagt gaacaacctc tatttggtgc aggttctatt     1800
agtagcggtg aactttatat agataaaatt gaaattattc tagcagatgc aacatttgaa     1860
gcagaatctg atttagaaag agcacaaaag gcggtgaatg ccctgtttac ttcttccaat     1920
caaatcgggt taaaaaccga tgtgacggat tatcatattg atcaagtatc caatttagtg     1980
gattgtttat cagatgaatt ttgtctggat gaaaagcgag aattgtccga gaaagtcaaa     2040
catgcgaagc gactcagtga tgagcggaat ttacttcaag atccaaactt cagagggatc     2100
aatagacaac cagaccgtgg ctggagagga agtacagata ttaccatcca aggaggagat     2160
gacgtattca aagagaatta cgtcacacta ccgggtaccg ttgatgagtg ctatccaacg     2220
tatttatatc agaaaataga tgagtcgaaa ttaaaagctt atacccgtta tgaattaaga     2280
gggtatatcg aagatagtca agacttagaa atctatttga tccgttacaa tgcaaaacac     2340
gaaatagtaa atgtgccagg cacgggttcc ttatggccgc tttcagccca aagtccaatc     2400
ggaaagtgtg gagaaccgaa tcgatgcgcg ccacaccttg aatggaatcc tgatctagat     2460
tgttcctgca gagacgggga aaaatgtgca catcattccc atcatttcac cttggatatt     2520
gatgttggat gtacagactt aaatgaggac ttaggtctat gggtgatatt caagattaag     2580
acgcaagata accatgcaag actagggaat ctagagtttc tcgaagagaa accattatta     2640
ggggaagcac tagctcgtgt gaaaagagcg gagaagaagt ggagagacaa acgagagaaa     2700
ctgcagttgg aaacaaatat tgtttataaa gaggcaaaag aatctgtaga tgctttattt     2760
gtaaactctc aatatgatag attacaagtg aatacgaaca tcgcaatgat tcatgcggca     2820
gataaacgcg ttcatagaat ccgggaagcg tatctgccag agttgtctgt gattccaggt     2880
gtcaatgcgg ccatttcga agaattagag ggacgtattt ttacagcgta ttccttatat      2940
gatgcgagaa atgtcattaa aaatggcgat ttcaataatg gcttattatg ctggaacgtg     3000
aaaggtcatg tagatgtaga agagcaaaac aaccaccgtt cggtccttgt tatcccagaa     3060
tgggaggcag aagtgtcaca agaggttcgt gtctgtccag gtcgtggcta tatccttcgt     3120
gtcacagcat ataaagaggg atatggagag ggctgcgtaa cgatccatga gatcgaagac     3180
aatacagacg aactgaaatt cagcaactgt gtagaagagg aagtatatcc aaacaacaca     3240
```

-continued

```
gtaacgtgta ataattatac tgggactcaa gaagaatatg agggtacgta cacttctcgt    3300
aatcaaggat atgacgaagc ctatggtaat aacccttccg taccagctga ttacgcttca    3360
gtctatgaag aaaaatcgta tacagatgga cgaagagaga atccttgtga atctaacaga    3420
ggctatgggg attacacacc actaccggct ggttatgtaa caaaggattt agagtacttc    3480
ccagagaccg ataaggtatg gattgagatc ggagaaacag aaggaacatt catcgtggat    3540
agcgtggaat tactccttat ggaggaa                                        3567
```

<210> SEQ ID NO 6
<211> LENGTH: 1189
<212> TYPE: PRT
<213> ORGANISM: Bacillus thuringiensis

<400> SEQUENCE: 6

```
Met Glu Glu Asn Asn Gln Asn Gln Cys Ile Pro Tyr Asn Cys Leu Ser
1               5                   10                  15

Asn Pro Glu Glu Val Leu Leu Asp Gly Glu Arg Ile Ser Thr Gly Asn
                20                  25                  30

Ser Ser Ile Asp Ile Ser Leu Ser Leu Val Gln Phe Leu Val Ser Asn
            35                  40                  45

Phe Val Pro Gly Gly Gly Phe Leu Val Gly Leu Ile Asp Phe Val Trp
        50                  55                  60

Gly Ile Val Gly Pro Ser Gln Trp Asp Ala Phe Leu Val Gln Ile Glu
65                  70                  75                  80

Gln Leu Ile Asn Glu Arg Ile Ala Glu Phe Ala Arg Asn Ala Ala Ile
                85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Asn Asn Pro Ala Thr Arg Thr Arg
        115                 120                 125

Val Ile Asp Arg Phe Arg Ile Leu Asp Gly Leu Leu Glu Arg Asp Ile
130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
        275                 280                 285

Val Met Glu Ser Ser Ala Ile Arg Asn Pro His Leu Phe Asp Ile Leu
    290                 295                 300

Asn Asn Leu Thr Ile Phe Thr Asp Trp Phe Ser Val Gly Arg Asn Phe
305                 310                 315                 320
```

-continued

```
Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
            340                 345                 350

Ser Phe Thr Phe Asn Gly Pro Val Phe Arg Thr Leu Ser Asn Pro Thr
        355                 360                 365

Leu Arg Leu Leu Gln Gln Pro Trp Pro Ala Pro Pro Phe Asn Leu Arg
    370                 375                 380

Gly Val Glu Gly Val Glu Phe Ser Thr Pro Thr Asn Ser Phe Thr Tyr
385                 390                 395                 400

Arg Gly Arg Gly Gln Val Asp Ser Leu Thr Glu Leu Pro Pro Glu Asp
                405                 410                 415

Asn Ser Val Pro Pro Arg Glu Gly Tyr Ser His Arg Leu Cys His Ala
            420                 425                 430

Thr Phe Val Gln Arg Ser Gly Thr Pro Phe Leu Thr Thr Gly Val Val
        435                 440                 445

Phe Ser Trp Thr His Arg Ser Ala Thr Leu Thr Asn Thr Ile Asp Pro
    450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
            500                 505                 510

Ser Pro Ile Thr Gln Arg Tyr Arg Leu Arg Phe Arg Tyr Ala Ser Ser
        515                 520                 525

Arg Asp Ala Arg Val Ile Val Leu Thr Gly Ala Ala Ser Thr Gly Val
    530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
            580                 585                 590

Pro Leu Phe Gly Ala Gly Ser Ile Ser Ser Gly Glu Leu Tyr Ile Asp
        595                 600                 605

Lys Ile Glu Ile Ile Leu Ala Asp Ala Thr Phe Glu Ala Glu Ser Asp
    610                 615                 620

Leu Glu Arg Ala Gln Lys Ala Val Asn Ala Leu Phe Thr Ser Ser Asn
625                 630                 635                 640

Gln Ile Gly Leu Lys Thr Asp Val Thr Asp Tyr His Ile Asp Gln Val
                645                 650                 655

Ser Asn Leu Val Asp Cys Leu Ser Asp Glu Phe Cys Leu Asp Glu Lys
            660                 665                 670

Arg Glu Leu Ser Glu Lys Val Lys His Ala Lys Arg Leu Ser Asp Glu
        675                 680                 685

Arg Asn Leu Leu Gln Asp Pro Asn Phe Arg Gly Ile Asn Arg Gln Pro
    690                 695                 700

Asp Arg Gly Trp Arg Gly Ser Thr Asp Ile Thr Ile Gln Gly Gly Asp
705                 710                 715                 720

Asp Val Phe Lys Glu Asn Tyr Val Thr Leu Pro Gly Thr Val Asp Glu
                725                 730                 735
```

-continued

```
Cys Tyr Pro Thr Tyr Leu Tyr Gln Lys Ile Asp Glu Ser Lys Leu Lys
            740                 745                 750

Ala Tyr Thr Arg Tyr Glu Leu Arg Gly Tyr Ile Glu Asp Ser Gln Asp
            755                 760                 765

Leu Glu Ile Tyr Leu Ile Arg Tyr Asn Ala Lys His Glu Ile Val Asn
            770                 775                 780

Val Pro Gly Thr Gly Ser Leu Trp Pro Leu Ser Ala Gln Ser Pro Ile
785                 790                 795                 800

Gly Lys Cys Gly Glu Pro Asn Arg Cys Ala Pro His Leu Glu Trp Asn
                    805                 810                 815

Pro Asp Leu Asp Cys Ser Cys Arg Asp Gly Glu Lys Cys Ala His His
                820                 825                 830

Ser His His Phe Thr Leu Asp Ile Asp Val Gly Cys Thr Asp Leu Asn
            835                 840                 845

Glu Asp Leu Gly Leu Trp Val Ile Phe Lys Ile Lys Thr Gln Asp Asn
850                 855                 860

His Ala Arg Leu Gly Asn Leu Glu Phe Leu Glu Glu Lys Pro Leu Leu
865                 870                 875                 880

Gly Glu Ala Leu Ala Arg Val Lys Arg Ala Glu Lys Lys Trp Arg Asp
                885                 890                 895

Lys Arg Glu Lys Leu Gln Leu Glu Thr Asn Ile Val Tyr Lys Glu Ala
                900                 905                 910

Lys Glu Ser Val Asp Ala Leu Phe Val Asn Ser Gln Tyr Asp Arg Leu
            915                 920                 925

Gln Val Asn Thr Asn Ile Ala Met Ile His Ala Ala Asp Lys Arg Val
            930                 935                 940

His Arg Ile Arg Glu Ala Tyr Leu Pro Glu Leu Ser Val Ile Pro Gly
945                 950                 955                 960

Val Asn Ala Ala Ile Phe Glu Glu Leu Glu Gly Arg Ile Phe Thr Ala
                965                 970                 975

Tyr Ser Leu Tyr Asp Ala Arg Asn Val Ile Lys Asn Gly Asp Phe Asn
            980                 985                 990

Asn Gly Leu Leu Cys Trp Asn Val  Lys Gly His Val Asp Val Glu Glu
            995                 1000                1005

Gln Asn Asn His Arg Ser Val  Leu Val Ile Pro Glu  Trp Glu Ala
    1010                1015                1020

Glu Val  Ser Gln Glu Val  Arg Val Cys Pro Gly Arg  Gly Tyr Ile
    1025                1030                1035

Leu Arg Val Thr Ala Tyr Lys  Glu Gly Tyr Gly Glu  Gly Cys Val
    1040                1045                1050

Thr Ile His Glu Ile Glu Asp  Asn Thr Asp Glu Leu  Lys Phe Ser
    1055                1060                1065

Asn Cys Val Glu Glu Glu Val  Tyr Pro Asn Asn Thr  Val Thr Cys
    1070                1075                1080

Asn Asn Tyr Thr Gly Thr Gln  Glu Glu Tyr Glu Gly  Thr Tyr Thr
    1085                1090                1095

Ser Arg Asn Gln Gly Tyr Asp  Glu Ala Tyr Gly Asn  Asn Pro Ser
    1100                1105                1110

Val Pro Ala Asp Tyr Ala Ser  Val Tyr Glu Glu Lys  Ser Tyr Thr
    1115                1120                1125

Asp Gly Arg Arg Glu Asn Pro  Cys Glu Ser Asn Arg  Gly Tyr Gly
    1130                1135                1140

Asp Tyr Thr Pro Leu Pro Ala  Gly Tyr Val Thr Lys  Asp Leu Glu
```

-continued

```
            1145                1150                1155
    Tyr Phe Pro Glu Thr Asp Lys Val Trp Ile Glu Ile Gly Glu Thr
                        1160                1165                1170
    Glu Gly Thr Phe Ile Val Asp Ser Val Glu Leu Leu Leu Met Glu
            1175                1180                1185
    Glu
```

<210> SEQ ID NO 7
<211> LENGTH: 3522
<212> TYPE: DNA
<213> ORGANISM: Bacillus thuringiensis

<400> SEQUENCE: 7

| | | |
|---|---|---|
| atggagaata atattcaaaa tcaatgcgta ccttacaatt gtttaaataa tcctgaagta | 60 |
| gaaatattaa atgaagaaag aagtactggc agattaccgt tagatatatc cttatcgctt | 120 |
| acacgtttcc ttttgagtga atttgttcca ggtgtgggag ttgcgtttgg attatttgat | 180 |
| ttaatatggg gttttataac tccttctgat tggagcttat ttcttttaca gattgaacaa | 240 |
| ttgattgagc aaagaataga aacattggaa aggaaccggg caattactac attacgaggg | 300 |
| ttagcagata gctatgaaat ttatattgaa gcactaagag agtgggaagc aaatcctaat | 360 |
| aatgcacaat taagggaaga tgtgcgtatt cgatttgcta atacagacga cgctttaata | 420 |
| acagcaataa ataattttac acttacaagt tttgaaatcc ctctttttatc ggtctatgtt | 480 |
| caagcggcga atttacattt atcactatta agagacgctg tatcgtttgg gcagggttgg | 540 |
| ggactggata tagctactgt taataatcat tataatagat taataaatct tattcataga | 600 |
| tatacgaaac attgtttgga cacatacaat caaggattag aaaacttaag aggtactaat | 660 |
| actcgacaat gggcaagatt caatcagttt aggagagatt taacacttac tgtattagat | 720 |
| atcgttgctc ttttttccgaa ctacgatgtt agaacatatc caattcaaac gtcatcccaa | 780 |
| ttaacaaggg aaatttatac aagttcagta attgaggatt ctccagtttc tgctaatata | 840 |
| cctaatggtt ttaataggc ggaatttgga gttagaccgc ccatcttat ggactttatg | 900 |
| aattctttgt tgtaactgc agagactgtt agaagtcaaa ctgtgtgggg aggacactta | 960 |
| gttagttcac gaaatacggc tggtaaccgt ataaatttcc ctagttacgg ggtcttcaat | 1020 |
| cctggtggcg ccatttggat tgcagatgag gatccacgtc ttttttatcg gacattatca | 1080 |
| gatcctgttt tgtccgagg aggatttggg aatcctcatt atgtactggg gcttagggga | 1140 |
| gtagcatttc aacaaactgg tacgaaccac acccgaacat ttagaaatag tgggaccata | 1200 |
| gattctctag atgaaatccc acctcaggat aatagtgggg gccacttggaa tgattatagt | 1260 |
| catgtattaa atcatgttac atttgtacga tggccaggtg agatttcagg aagtgattca | 1320 |
| tggagagctc caatgttttc ttggacgcac cgtagtgcaa cccctacaaa tacaattgat | 1380 |
| ccggagagga ttactcaaat accattggta aaagcacata cacttcagtc aggtactact | 1440 |
| gttgtaagag ggcccggtt tacgggagga gatattcttc gacgaacaag tggaggacca | 1500 |
| tttgcttata ctattgttaa tataaatggg caattacccc aaaggtatcg tgcaagaata | 1560 |
| cgctatgcct ctactacaaa tctaagaatt tacgtaacgg ttgcaggtga acggattttt | 1620 |
| gctggtcaat ttaacaaaac aatggatacc ggtgacccat taacattcca atcttttagt | 1680 |
| tacgcaacta ttaatacagc ttttacattc ccaatgagcc agagtagttt cacagtaggt | 1740 |
| gctgatactt ttagttcagg gaatgaagtt tatatagaca gatttgaatt gattccagtt | 1800 |
| actgcaacat tgaagcaga atatgattta gaaagagcac aaaaggcggt gaatgcgctg | 1860 |

-continued

```
tttacttcta taaaccaaat agggataaaa acagatgtga cggattatca tattgatcaa   1920
gtatccaatt tagtggattg tttatcagat gaattttgtc tggatgaaaa gcgagaattg   1980
tccgagaaag tcaaacatgc gaagcgactc agtgatgagc ggaatttact tcaagatcca   2040
aacttcaaag gcatcaatag gcaactagac cgtggttgga gaggaagtac ggatattacc   2100
atccaaagag gagatgacgt attcaaagaa aattatgtca cactaccagg tacctttgat   2160
gagtgctatc caacgtattt atatcaaaaa atagatgagt cgaaattaaa accctatact   2220
cgttatcaat taagagggta tatcgaggat agtcaagact tagaaatcta tttgatccgc   2280
tataatgcaa aacacgaaac agtaaatgtg ctaggtacgg gttctttatg gccgctttca   2340
gtccaaagtc caatcagaaa gtgtggagaa ccgaatcgat gcgcgccaca ccttgaatgg   2400
aatcctgatc tagattgttc ctgcagagac ggggaaaaat gtgcacatca ttcgcatcat   2460
ttctccttgg acattgatgt tggatgtaca gacttaaatg aggacttaga tgtatgggtg   2520
atattcaaga ttaagacgca agatggccat gcaagactag gaaatctaga gtttctcgaa   2580
gagaaaccat tagtcgggga agcactagct cgtgtgaaaa gagcagagaa aaaatggaga   2640
gataaacgtg aaaaattgga attggaaaca aatattgttt ataaagaggc aaaagaatct   2700
gtagatgctt tatttgtaaa ctctcaatat gatcaattac aagcggatac gaatattgcc   2760
atgattcatg cggcagataa acgtgttcat agaattcggg aagcgtatct tccagagtta   2820
tctgtgattc cgggtgtaaa tgtagacatt ttcgaagaat taaaagggcg tattttcact   2880
gcattcttcc tatatgatgc gagaaatgtc attaaaaacg gtgatttcaa taatggctta   2940
tcatgctgga acgtgaaagg gcatgtagat gtagaagaac aaaacaacca ccgttcggtc   3000
cttgttgttc cggaatggga agcagaagtg tcacaagaag ttcgtgtctg tccgggtcgt   3060
ggctatatcc ttcgtgtcac agcgtacaag gagggatatg gagaaggttg cgtaaccatt   3120
catgagatcg agaacaatac agacgaactg aagtttagca actgcgtaga agaggaagtc   3180
tatccaaaca acacggtaac gtgtaatgat tatactgcaa atcaagaaga atacgggggt   3240
gcgtacactt cccgtaatcg tggatatgac gaaacttatg gaagcaattc ttctgtacca   3300
gctgattatg cgtcagtcta tgaagaaaaa tcgtatacag atggacgaag agacaatcct   3360
tgtgaatcta acagaggata tggggattac acaccactac cagctggcta tgtgacaaaa   3420
gaattagagt acttcccaga aaccgataag gtatggattg agatcggaga aacggaagga   3480
acattcatcg tggacagcgt ggaattactc cttatggagg aa                      3522
```

<210> SEQ ID NO 8
<211> LENGTH: 1174
<212> TYPE: PRT
<213> ORGANISM: Bacillus thuringiensis

<400> SEQUENCE: 8

```
Met Glu Asn Asn Ile Gln Asn Gln Cys Val Pro Tyr Asn Cys Leu Asn
1               5                   10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

Phe Ile Thr Pro Ser Asp Trp Ser Leu Phe Leu Leu Gln Ile Glu Gln
65                  70                  75                  80
```

-continued

```
Leu Ile Glu Gln Arg Ile Glu Thr Leu Glu Arg Asn Arg Ala Ile Thr
                85                  90                  95
Thr Leu Arg Gly Leu Ala Asp Ser Tyr Glu Ile Tyr Ile Glu Ala Leu
            100                 105                 110
Arg Glu Trp Glu Ala Asn Pro Asn Asn Ala Gln Leu Arg Glu Asp Val
        115                 120                 125
Arg Ile Arg Phe Ala Asn Thr Asp Asp Ala Leu Ile Thr Ala Ile Asn
    130                 135                 140
Asn Phe Thr Leu Thr Ser Phe Glu Ile Pro Leu Leu Ser Val Tyr Val
145                 150                 155                 160
Gln Ala Ala Asn Leu His Leu Ser Leu Leu Arg Asp Ala Val Ser Phe
                165                 170                 175
Gly Gln Gly Trp Gly Leu Asp Ile Ala Thr Val Asn Asn His Tyr Asn
            180                 185                 190
Arg Leu Ile Asn Leu Ile His Arg Tyr Thr Lys His Cys Leu Asp Thr
        195                 200                 205
Tyr Asn Gln Gly Leu Glu Asn Leu Arg Gly Thr Asn Thr Arg Gln Trp
    210                 215                 220
Ala Arg Phe Asn Gln Phe Arg Arg Asp Leu Thr Leu Thr Val Leu Asp
225                 230                 235                 240
Ile Val Ala Leu Phe Pro Asn Tyr Asp Val Arg Thr Tyr Pro Ile Gln
                245                 250                 255
Thr Ser Ser Gln Leu Thr Arg Glu Ile Tyr Thr Ser Ser Val Ile Glu
            260                 265                 270
Asp Ser Pro Val Ser Ala Asn Ile Pro Asn Gly Phe Asn Arg Ala Glu
        275                 280                 285
Phe Gly Val Arg Pro Pro His Leu Met Asp Phe Met Asn Ser Leu Phe
    290                 295                 300
Val Thr Ala Glu Thr Val Arg Ser Gln Thr Val Trp Gly Gly His Leu
305                 310                 315                 320
Val Ser Ser Arg Asn Thr Ala Gly Asn Arg Ile Asn Phe Pro Ser Tyr
                325                 330                 335
Gly Val Phe Asn Pro Gly Gly Ala Ile Trp Ile Ala Asp Glu Asp Pro
            340                 345                 350
Arg Pro Phe Tyr Arg Thr Leu Ser Asp Pro Val Phe Val Arg Gly Gly
        355                 360                 365
Phe Gly Asn Pro His Tyr Val Leu Gly Leu Arg Gly Val Ala Phe Gln
    370                 375                 380
Gln Thr Gly Thr Asn His Thr Arg Thr Phe Arg Asn Ser Gly Thr Ile
385                 390                 395                 400
Asp Ser Leu Asp Glu Ile Pro Pro Gln Asp Asn Ser Gly Ala Pro Trp
                405                 410                 415
Asn Asp Tyr Ser His Val Leu Asn His Val Thr Phe Val Arg Trp Pro
            420                 425                 430
Gly Glu Ile Ser Gly Ser Asp Ser Trp Arg Ala Pro Met Phe Ser Trp
        435                 440                 445
Thr His Arg Ser Ala Thr Pro Thr Asn Thr Ile Asp Pro Glu Arg Ile
    450                 455                 460
Thr Gln Ile Pro Leu Val Lys Ala His Thr Leu Gln Ser Gly Thr Thr
465                 470                 475                 480
Val Val Arg Gly Pro Gly Phe Thr Gly Gly Asp Ile Leu Arg Arg Thr
                485                 490                 495
```

-continued

```
Ser Gly Gly Pro Phe Ala Tyr Thr Ile Val Asn Ile Asn Gly Gln Leu
            500                 505                 510
Pro Gln Arg Tyr Arg Ala Arg Ile Arg Tyr Ala Ser Thr Thr Asn Leu
            515                 520                 525
Arg Ile Tyr Val Thr Val Ala Gly Glu Arg Ile Phe Ala Gly Gln Phe
            530                 535                 540
Asn Lys Thr Met Asp Thr Gly Asp Pro Leu Thr Phe Gln Ser Phe Ser
545                 550                 555                 560
Tyr Ala Thr Ile Asn Thr Ala Phe Thr Phe Pro Met Ser Gln Ser Ser
                565                 570                 575
Phe Thr Val Gly Ala Asp Thr Phe Ser Ser Gly Asn Glu Val Tyr Ile
            580                 585                 590
Asp Arg Phe Glu Leu Ile Pro Val Thr Ala Thr Phe Glu Ala Glu Tyr
            595                 600                 605
Asp Leu Glu Arg Ala Gln Lys Ala Val Asn Ala Leu Phe Thr Ser Ile
            610                 615                 620
Asn Gln Ile Gly Ile Lys Thr Asp Val Thr Asp Tyr His Ile Asp Gln
625                 630                 635                 640
Val Ser Asn Leu Val Asp Cys Leu Ser Asp Glu Phe Cys Leu Asp Glu
                645                 650                 655
Lys Arg Glu Leu Ser Glu Lys Val Lys His Ala Lys Arg Leu Ser Asp
            660                 665                 670
Glu Arg Asn Leu Leu Gln Asp Pro Asn Phe Lys Gly Ile Asn Arg Gln
            675                 680                 685
Leu Asp Arg Gly Trp Arg Gly Ser Thr Asp Ile Thr Ile Gln Arg Gly
            690                 695                 700
Asp Asp Val Phe Lys Glu Asn Tyr Val Thr Leu Pro Gly Thr Phe Asp
705                 710                 715                 720
Glu Cys Tyr Pro Thr Tyr Leu Tyr Gln Lys Ile Asp Glu Ser Lys Leu
                725                 730                 735
Lys Pro Tyr Thr Arg Tyr Gln Leu Arg Gly Tyr Ile Glu Asp Ser Gln
            740                 745                 750
Asp Leu Glu Ile Tyr Leu Ile Arg Tyr Asn Ala Lys His Glu Thr Val
            755                 760                 765
Asn Val Leu Gly Thr Gly Ser Leu Trp Pro Leu Ser Val Gln Ser Pro
            770                 775                 780
Ile Arg Lys Cys Gly Glu Pro Asn Arg Cys Ala Pro His Leu Glu Trp
785                 790                 795                 800
Asn Pro Asp Leu Asp Cys Ser Cys Arg Asp Gly Glu Lys Cys Ala His
                805                 810                 815
His Ser His His Phe Ser Leu Asp Ile Asp Val Gly Cys Thr Asp Leu
            820                 825                 830
Asn Glu Asp Leu Asp Val Trp Val Ile Phe Lys Ile Lys Thr Gln Asp
            835                 840                 845
Gly His Ala Arg Leu Gly Asn Leu Glu Phe Leu Glu Glu Lys Pro Leu
            850                 855                 860
Val Gly Glu Ala Leu Ala Arg Val Lys Arg Ala Glu Lys Lys Trp Arg
865                 870                 875                 880
Asp Lys Arg Glu Lys Leu Glu Leu Glu Thr Asn Ile Val Tyr Lys Glu
                885                 890                 895
Ala Lys Glu Ser Val Asp Ala Leu Phe Val Asn Ser Gln Tyr Asp Gln
            900                 905                 910
Leu Gln Ala Asp Thr Asn Ile Ala Met Ile His Ala Ala Asp Lys Arg
```

-continued

```
                    915                 920                 925
Val His Arg Ile Arg Glu Ala Tyr Leu Pro Glu Leu Ser Val Ile Pro
    930                 935                 940

Gly Val Asn Val Asp Ile Phe Glu Glu Leu Lys Gly Arg Ile Phe Thr
945                 950                 955                 960

Ala Phe Phe Leu Tyr Asp Ala Arg Asn Val Ile Lys Asn Gly Asp Phe
                965                 970                 975

Asn Asn Gly Leu Ser Cys Trp Asn Val Lys Gly His Val Asp Val Glu
            980                 985                 990

Glu Gln Asn Asn His Arg Ser Val Leu Val Val Pro Glu Trp Glu Ala
        995                 1000                1005

Glu Val Ser Gln Glu Val Arg Val Cys Pro Gly Arg Gly Tyr Ile
    1010                1015                1020

Leu Arg Val Thr Ala Tyr Lys Glu Gly Tyr Gly Glu Gly Cys Val
    1025                1030                1035

Thr Ile His Glu Ile Glu Asn Asn Thr Asp Glu Leu Lys Phe Ser
    1040                1045                1050

Asn Cys Val Glu Glu Val Tyr Pro Asn Asn Thr Val Thr Cys
    1055                1060                1065

Asn Asp Tyr Thr Ala Asn Gln Glu Glu Tyr Gly Gly Ala Tyr Thr
    1070                1075                1080

Ser Arg Asn Arg Gly Tyr Asp Glu Thr Tyr Gly Ser Asn Ser Ser
    1085                1090                1095

Val Pro Ala Asp Tyr Ala Ser Val Tyr Glu Glu Lys Ser Tyr Thr
    1100                1105                1110

Asp Gly Arg Arg Asp Asn Pro Cys Glu Ser Asn Arg Gly Tyr Gly
    1115                1120                1125

Asp Tyr Thr Pro Leu Pro Ala Gly Tyr Val Thr Lys Glu Leu Glu
    1130                1135                1140

Tyr Phe Pro Glu Thr Asp Lys Val Trp Ile Glu Ile Gly Glu Thr
    1145                1150                1155

Glu Gly Thr Phe Ile Val Asp Ser Val Glu Leu Leu Leu Met Glu
    1160                1165                1170

Glu
```

<210> SEQ ID NO 9
<211> LENGTH: 42
<212> TYPE: DNA
<213> ORGANISM: Artificial Sequence
<220> FEATURE:
<223> OTHER INFORMATION: 42-mer oligonucleotide constructed to the
      sequence of the insert in pM2,31-4

<400> SEQUENCE: 9
ggataccggt gacccattaa cattccaatc ttttagttac gc                    42

<210> SEQ ID NO 10
<211> LENGTH: 40
<212> TYPE: DNA
<213> ORGANISM: Artificial Sequence
<220> FEATURE:
<223> OTHER INFORMATION: 40-mer oligonucleotide constructed to the
      sequence of the insert in pM2,31-1

<400> SEQUENCE: 10
gaagtttatg gcctctttct gtagaaaatc aaattggacc                       40

BACILLUS THURINGIENSIS ISOLATE ACTIVE AGAINST LEPIDOPTERAN PESTS, AND GENES ENCODING NOVEL LEPIDOPTERAN-ACTIVE TOXINS

CROSS-REFERENCE TO A RELATED APPLICATION

This is a divisional of application Ser. No. 09/521,344, filed Mar. 9, 2000 now U.S. Pat. No. 6,573,240; which is a divisional of application Ser. No. 08/933,891, filed Sep. 19, 1997, now U.S. Pat. No. 6,096,708; which is a continuation of application Ser. No. 08/356,034, filed Dec. 14, 1994, now U.S. Pat. No. 5,691,308; which is a continuation of Ser. No. 08/210,110, filed Mar. 17, 1994, now abandoned; which is a continuation of Ser. No. 07/865,168, filed Apr. 9, 1992, now abandoned; which is a division of Ser. No. 07/451,261, filed Dec. 14, 1989, now U.S. Pat. No. 5,188,960; which is a continuation-in-part of Ser. No. 371,955, filed Jun. 27, 1989, now U.S. Pat. No. 5,126,133.

BACKGROUND OF THE INVENTION

The most widely used microbial pesticides are derived from the bacterium *Bacillus thuringiensis*. This bacterial agent is used to control a wide range of leaf-eating caterpillars and beetles, as well as mosquitos. *Bacillus thuringiensis* produces a proteinaceous parasporal body or crystal which is toxic upon ingestion by a susceptible insect host. For example, *B. thuringiensis* subsp. *kurstaki* HD-1 produces a crystal inclusion consisting of a biotoxin called a delta toxin which is toxic to the larvae of a number of lepidopteran insects. The cloning, sequencing, and expression of this *B.t.* crystal protein gene in *Escherichia coli* has been described in the published literature (Schnepf, H. E. and Whitely, H. R. [1981] Proc. Natl. Acad. Sci. USA 78:2893–2897; Schnepf et al.). U.S. Pat. No. 4,448,885 and U.S. Pat. No. 4,467,036 both disclose the expression of *B.t.* crystal protein in *E. coli*.

BRIEF SUMMARY OF THE INVENTION

The subject invention concerns a novel *Bacillus thuringiensis* isolate designated *B.t.* PS81I which has activity against all lepidopteran pests tested.

Also disclosed and claimed are novel toxin genes which express toxins toxic to lepidopteran insects. These toxin genes can be transferred to suitable hosts via a plasmid vector.

Specifically, the invention comprises the novel *B.t.* isolate denoted *B.t.* PS81I, mutants thereof, and novel δ-endotoxin genes derived from this *B.t.* isolate which encode proteins which are active against lepidopteran pests.

BRIEF DESCRIPTION OF THE SEQUENCES

SEQ ID NO:1 is the nucleotide sequence of the novel *B.t.* toxin gene PS81I2.

SEQ ID NO:2 is the amino acid sequence of the novel *B.t.* toxin PS81IA2.

SEQ ID NO:3 is the nucleotide sequence of the novel *B.t.* toxin gene PS81B.

SEQ ID NO:4 is the amino acid sequence of the novel *B.t.* toxin PS81B.

SEQ ID NO:5 is the nucleotide sequence of the novel *B.t.* toxin gene PS81IB2.

SEQ ID NO:6 is the amino acid sequence of the novel *B.t.* toxin PS81IB2.

SEQ ID NO:7 is the nucleotide sequence of the novel *B.t.* toxin gene PS81IA.

SEQ ID NO:8 is the amino acid sequence of the novel *B.t.* toxin PS81IA.

SEQ ID NO:9 is the 42-mer oligonucleotide constructed to the sequence of the insert in pM2,31-4.

SEQ ID NO:10 is the 40-mer oligonucleotide constructed to the sequence of the insert in pM2,31-1.

BRIEF DESCRIPTION OF THE DRAWINGS

FIG. 1—agarose gel electrophoresis of plasmid preparations from *B.t.* HD-1 and *B.t.* PS81I.

DETAILED DISCLOSURE OF THE INVENTION

The novel toxin genes of the subject invention were obtained from a novel lepidopteran-active *B. thuringiensis* (*B.t.*) isolate designated PS81I.

Characteristics of *B.t.* PS81I

Colony morphology—Large colony, dull surface, typical *B.t.*

Vegetative cell morphology—typical *B.t.*

Flagellar serotype—7, aizawai.

Intracellular inclusions—sporulating cells produce a bipyrarnidal crystal.

Plasmid preparations—agarose gel electrophoresis of plasmid preparations distinguishing *B.t.* PS81I from *B.t.* HD-1. See FIG. 1.

Alkali-soluble proteins—SDS-PAGE analysis shows a protein band at ca. 130,000 daltons.

Unique toxins—four unique toxins have been identified in *B.t.* PS81I.

Activity—*B.t.* PS81I kills all Lepidoptera tested.

Bioassay procedures:

*B.t.* PS81I spores and crystals were tested against: Beet Armyworm, *Spodoptera exigua*; Diamondback Moth, *Plutella xylostella*; Western Spruce Budworm, *Choristoneura occidentalis*.

LC50 values were as follows:

Beet Armyworm—2.53 ppm

Diamondback Moth—0.16 ppm

Western Spruce Budworm—3.2 ppm

Bioassay procedure: dilutions are prepared of a spore and crystal pellet, mixed with USDA Insect Diet (Technical Bulletin 1528, U.S. Department of Agriculture), and poured into small plastic trays. Larvae are placed on the diet mixture and held at 25° C. (late 2nd instar Diamondback Moth larvae, early 2nd instar Beet Armyworm larvae, 4th instar Western Spruce Budworm larvae). Mortality is recorded after six days.

*B. thuringiensis* PS81I, NRRL B-18484, and mutants thereof, can be cultured using standard known media and fermentation techniques. Upon completion of the fermentation cycle, the bacteria can be harvested by first separating the *B.t.* spores and crystals from the fermentation broth by means well known in the art. The recovered *B.t.* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against Lepidoptera, e.g., caterpillars. *B.t.* PS81I, and mutants thereof, can be used to control lepidopteran pests.

A subculture of *B.t.* PS81I and the *E. coli* hosts harboring the toxin genes of the invention, were deposited in the permanent collection of the Northern Research Laboratory, U.S. Department of Agriculture, Peoria, Ill., USA. The accession numbers and deposit dates are as follows:

| Subculture | Accession Number | Deposit Date |
| --- | --- | --- |
| *B.t.* PS81I | NRRL B-18484 | Apr. 19, 1989 |
| *E. coli*(NM522)(pMYC392) | NRRL B-18498 | May 17, 1989 |
| *E. coli*(NM522)(pMYC393) | NRRL B-18499 | May 17, 1989 |
| *E. coli*(NM522)(pMYC394) | NRRL B-18500 | May 17, 1989 |
| *E. coli*(NM522)(pMYC1603) | NRRL B-18517 | Jun. 30, 1989 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing these.

The toxin genes of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be If applied to the environment of target pest(s). The resulting product retains the toxicity of the *B.t.* toxin.

Where the *B.t.* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Bacillus, Pseudomonas, Erwinia, Serratia, Klebsiella, Xanthomonas, Streptomyces, Rhizobium, Rhodopseudomonas, Methylophilius, Azrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A wide variety of ways are available for introducing a *B.t.* gene expressing a toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratig Aeromonas, Vibrio, Desulfovibrio, Spirillum, Lactobacillaceae; Pseudomonadaceae, such as Pseudomonas and Acetobacter; Azotobacteraceae, Actinomycetales, and Nitrobacteraceae, Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., Streptomyces sp., and the like. Specific organisms include *Pseudomonas aeruginosa, Pseudomonas fluorescens, Saccharomyces cerevisiae, Bacillus thuringiensis, Escherichia coli, Bacillus subtilis, Streptomyces lividans* and the like.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., Animal Tissue Techniques, W.H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Mutants of PS81I can be made by procedures well known in the art. For example, an asporogenous mutant can be obtained through ethylmethane sulfonate (EMS) mutagenesis of PS81I. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *B.t.* PS81I

A subculture of *B.t.* PS81I, or mutants thereof, can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

EXAMPLE 2

Cloning of Novel Toxin Genes From Isolate PS81I and Transformation Into *Escherichia coli*

Total cellular DNA was prepared from B.t. cells grown to a low optical density ($OD_{600}$=1.0). The cells were recovered by centrifugation and protoplasted in TES buffer (30 mM Tris-Cl, 10 mM ethylenediaminetetraacetic acid [EDTA], 50 mM NaCl, pH=8.0) containing 20% sucrose and 50 mg/ml lysozyme. The protoplasts were lysed by addition of sodium dodecyl sulfate (SDS) to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium gradient.

Total cellular DNA from PS81I and *B.t.k.* HD-1 was digested with EcoRI and separated by electrophoresis on a 0.8% (w/v) Agarose-TAE (50 mM Tris-Cl, 20 mM NaOAc, 2.5 mM EDTA, pH=8.0) buffered gel. A Southern blot of the gel was hybridized with a [$^{32}$P] radiolabeled probe against the 3.2 Kb NsiI to NsiI fragment of the toxin gene contained in plasmid pM3,130-7 of NRRL B-18332 and the 2.4 Kb NsiI to KpnI fragment of the "4.5 Kb class" toxin gene (Kronstad and Whitely [1986] Gene USA 43:29–40). These two fragments were combined and used as the probe. Results show that hybridizing fragments of PS81I are distinct from those of HD-1. Specifically, in the 1.5 Kb to 2.5 Kb size range, 2.3 Kb, 1.95 Kb, and 1.6 Kb hybridizing bands were detected in PS81I instead of the single 1.9 Kb hybridizing band in HD-1.

The following description outlines the steps taken in cloning two of the three EcoRI fragments described above. Two hundred micrograms of PS81I total cellular DNA was digested with EcoRI and separated by electrophoresis on a preparative 0.8% (w/v) Agarose-TAE gel. The 1.5 Kb to 2.3 Kb region of the gel was cut out and the DNA from it was electroeluted and concentrated using an ELUTIP™–d (Schleicher and Schuell, Keene, N. H.) ion exchange column according to the manufacturer's specification. The isolated EcoRI fragments were ligated to LAMBDA ZAP™ EcoRI arms (Stratagene Cloning Systems, La Jolla, Calif.) and packaged using Gigapak GOLD™ (Stratagene) extracts. The packaged recombinant phage were plated with *E. coli* strain BB4 (Stratagene) to give high plaque density. The plaques were screened by standard nucleic acid hybridization procedures with radiolabeled probe. The plaques that hybridized were purified and re-screened at a lower plaque density. The resulting purified phage were grown with R408 M13 helper phage (Stratagene) and the recombinant BlueScript™ (Stratagene) plasmid was automatically excised and packaged. The "phagemid" was re-infected in XL1-Blue *E. coli* cells (Stratagene) as part of the automatic excision process. The infected XL1-Blue cells were screened for ampicillin resistance and the resulting colonies were analyzed by a standard rapid plasmid purification procedure to identify the desired plasmids. The plasmids, designated pM2,31-4 and pM2,31-1, contain approximately 1.95 Kb and 1.6 Kb EcoRI inserts, respectively. The DNA sequence of both inserts was determined using Stratagene's T7 and T3 oligonucleotide primers plus a set of existing internal *B.t.* endotoxin gene oligonucleotide primers. About 500 bp of the insert in pM2,31-4 was sequenced. In the same manner, approximately 1.0 Kb of the insert in pM2,31-1 was sequenced. Data analysis comparing the two sequences to other cloned and sequenced *B.t.* endotoxin genes showed that two distinct, unique partial toxin gene sequences had been found. Synthetic oligonucleotides were constructed to regions in both sequences that had minimum homology to other characterized *B.t.* endotoxin genes. The 42-mer oligonucleotide constructed to the sequence of the insert in pM2,31-4 was GGATACCGGTGACCCATTAACATTC-CAATCT TTTAGTTACGC; it was used to isolate a toxin gene sequence called 81IA. The 40-mer oligonucleotide constructed to the sequence of the insert in pM2,31-1 was GAAGTTTATGG CCTCTTTCTGTAGAAAATCAAAT-TGGACC; it was used to isolate a toxin gene sequence called 81IB.

In order to clone both complete toxin genes, a Sau3A partial library was constructed. PS81I total cellular DNA partially digested with Sau3A and size fractionated by electrophoresis into a mixture of 9–23 Kb fragments on a 0.6% agarose-TAE gel, and purified as described previously, was ligated into LambdaGEM-11™ (PROMEGA). The packaged phage were plated on P2392 *E. coli* cells (Stratagene) at a high titer and screened using the radiolabeled synthetic oligonucleotides (aforementioned) as nucleic acid hybridization probes. Hybridizing plaques, using each probe, were rescreened at a lower plaque density. Purified plaques that hybridized with either probe were used to infect P2392 *E. coli* cells in liquid culture for preparation of phage for DNA isolation. DNA was isolated by standard procedures. Preparative amounts of DNA were digested with SalI (to release the inserted DNA from lambda arms) and separated by electrophoresis on a 0.6% agarose-TAE gel. The large fragments, electroeluted and concentrated as described above, were ligated to SalI-digested and dephosphorylated pUC19 (NEB). The ligation mix was introduced by transformation into DH5(α) competent *E. coli* cells (BRL) and plated on LB agar containing ampicillin, isopropyl-(β)-D-thiogalactoside (IPTG), and 5-bromo-4-chloro-3-indolyl-(β)-D-galactoside (XGAL). White colonies, with prospective insertions in the (β)-galactosidase gene of pUC19, were subjected to standard rapid plasmid purification procedures to isolate the desired plasmids. Plasmid pM3,122-1 contains a 15 Kb Sau3A fragment isolated using the 81IA oligonucleotide probe. Plasmid pM4,59-1 contains an 18 Kb Sau3A fragment isolated using the 81IB oligonucleotide probe.

Plasmid pM3,122-1 was digested with several restriction enzymes and Southern blotted. The blot was probed with the [$^{32}$P] radiolabeled 81IA specific oligonucleotide probe, as well as the labeled oligonucleotide sequencing primers made to known *B.t.k.* toxin genes. The resulting autoradiogram showed that two toxin genes were present in tandem on this cloned Sau3A fragment. Plasmid pM3,122-1 had a 4.0 Kb NdeI fragment that hybridized with oligonucleotide probes made to known *B.t.k.* genes. This fragment, however, did not hybridize with the specific oligonucleotides to 81IA or 81IB; a new toxin gene had been discovered and subsequently was called 81IA2. The 4.0 Kb NdeI fragment was isolated and cloned in pUC19, yielding plasmid pMYC392. The 81IA toxin gene was isolated by digesting pM3,122-1 with HindIII, with resulting deletion of most of the 81IA2 toxin gene. The fragment was recircularized to form pMYC1603.

The 81IA toxin gene is unique based on its restriction map and its DNA sequence.

Plasmid pM4,59-1 was digested with several restriction enzymes and Southern blotted. The blot was probed with the [$^{32}$P] radiolabeled 81IB specific oligonucleotide probe, as well as with labeled oligonucleotide sequencing primers made to known *B.t.k.* toxin genes. The plasmid pM4,59-1 was mapped and found to contain only a partial 81IB toxin gene. The full open reading frame (ORF) of a second toxin gene was discovered on the 18 Kb fragment and called 81IB2. The 81IB2 toxin gene was cloned separately from the 81IB toxin gene by digestion of pM4,59-1 with NdeI and SmaI, filling in the NdeI overhang and ligating the linear fragment back together. The resulting plasmid was called pMYC394. The full ORF of the 81IB toxin gene was isolated from another Sau3A fragment, cloned from the lambda library, on a 7.3 Kb HindIII fragment in pBluescript (Stratagene). The resulting plasmid is pMYC393.

The toxin genes were sequenced by the standard Sanger dideoxy chain termination method using oligonucleotide primers made to the "4.5 Kb class" toxin gene and by "walking" with primers made to the sequences of the new toxin genes. Sequence analysis of the four toxin genes has elucidated unique open reading frames and has deduced unique endotoxin proteins. The following table summarizes the size of each ORF in base pairs and the deduced endotoxin molecular weight in daltons.

| TOXIN GENE | ORF (bp) | DEDUCED MW (daltons) | SEQUENCES |
|---|---|---|---|
| 81IA2 | 3537 | 133,367 | SEQ ID NOs:1–2 |
| 81IB | 3495 | 132,480 | SEQ ID NOs:3–4 |
| 81IB2 | 3567 | 134,714 | SEQ ID NOs:5–6 |
| 81IA | 3716 | 133,621 | SEQ ID NOs:7–8 |

Endotoxin proteins have been expressed in Pseudomonas and/or Bacillus from the toxin genes. SDS-PAGE/Western blot analysis, using polyclonal antibodies directed against the "6.6 Kb" class toxin, verified that each gene encodes an immunoreactive protein of approximately 130,000 daltons. The toxin proteins encoded by the genes of the subject invention expressed in either a Bacillus or Pseudomonas host have activity against all lepidopteran insects tested: *Trichoplusia ni, Spodoptera exigua, Plutella xylostella,* and *Choristoneura occidentalis.*

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E. F., and Sambrook, J. (1982) *Molecular Cloning: A Laboratory Manual*, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., New England Biolabs, Beverly, Mass., or Boehringer-Mannheim, Indianapolis, Ind. The enzymes are used according to the instructions provided by the supplier.

The plasmids containing the *B.t.* toxin genes can be removed from the transformed host microbes by use of standard well-known procedures. For example, the host microbes can be subjected to cleared lysate isopycnic density gradient procedures, and the like, to recover the desired plasmid.

EXAMPLE 3

Insertion of Toxin Genes Into Plants

The novel genes coding for the novel insecticidal toxins, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983] Cell 32:1033–1043). A particularly useful vector in this regard is pEND4K (Klee, H. J., Yanofsky, M. F. and Nester, E. W. [1985] Bio/Technology 3:637–642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 4

Cloning of Novel *B. thuringiensis* Genes Into Baculoviruses

The novel genes of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol Cell. Biol. 3:2156–2165). The gene coding for the novel protein toxin of the invention can be modified with BamHI linkers at appropriate regions both upstream and downstream from the coding region and inserted into the passenger site of one of the AcNPV vectors.

As disclosed previously, the nucleotide sequences encoding the novel *B.t.* toxin genes are shown in SEQ ID NO:1, SEQ ID NO:3, SEQ ID NO:5, and SEQ ID NO:7. The deduced amino acid sequences are shown in SEQ ID NO:2, SEQ ID NO:4, SEQ ID NO:6, and SEQ ID NO:8.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |

-continued

| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A=adenine
G=guanine
C=cytosine
T=thymine
X=T or C if Y is A or G
X=C if Y is C or T
Y=A, G, C or T if X is C
Y=A or G if X is T
W=C or A if Z is A or G
W=C if Z is C or T
Z=A, G, C or T if W is C
Z=A or G if W is A
QR=TC if S is A, G, C or T; alternatively QR=AG if S is T or C
J=A or G
K=T or C
L=A, T, C or G
M=A, C or T The above shows that the novel amino acid sequences of the *B.t.* toxins can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is retained to some degree.

What is claimed is:

1. An isolated polynucleotide that encodes a *Bacillus thuringiensis* toxin comprising an insecticidal fragment of SEQ ID NO:8.

2. The isolated polynucleotide according to claim 1 wherein said polynucleotide comprises a fragment of the nucleotide sequence of SEQ ID NO:7 sufficient to encode an insecticidal toxin.

3. A recombinant microbial or plant cell comprising an isolated polynucleotide sequence that encodes a toxin comprising an insecticidal fragment of SEQ ID NO:8.

4. The recombinant microbial or plant cell according to claim 3 wherein said polynucleotide comprises a fragment of the nucleotide sequence of SEQ ID NO:7 sufficient to encode an insecticidal toxin.

* * * * *

UNITED STATES PATENT AND TRADEMARK OFFICE
CERTIFICATE OF CORRECTION

PATENT NO. : 6,737,273 B2
DATED : May 18, 2004
INVENTOR(S) : Jewel Payne and August J. Sick It is certified that error appears in the above-identified patent and that said Letters Patent is hereby corrected as shown below:

Column 1,
Line 56, "toxin gene PS81I2" should read -- toxin gene PS81IA2 --

Column 3,
Line 51, "then can be If applied" should read -- then can be applied --

Column 6,
Line 37, "Nitrobacteraceae, Among" should read -- Nitrobacteraceae. Among --

Signed and Sealed this

Sixteenth Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,737,273 B2  Page 1 of 1
APPLICATION NO. : 09/837961
DATED : May 18, 2004
INVENTOR(S) : Jewel Payne and August J. Sick It is certified that error appears in the above-identified patent and that said Letters Patent is hereby corrected as shown below:

<u>Title Page</u>:
Item 73, Assignee, "Myocogen Corporation" should read --Mycogen Corporation--.

Signed and Sealed this

Fourth Day of November, 2008

JON W. DUDAS
*Director of the United States Patent and Trademark Office*